(12) United States Patent
Komura

(10) Patent No.: US 11,185,268 B2
(45) Date of Patent: *Nov. 30, 2021

(54) INFORMATION PROCESSING APPARATUS AND NON-TRANSITORY COMPUTER READABLE MEDIUM

(71) Applicant: FUJIFILM Business Innovation Corp., Tokyo (JP)

(72) Inventor: Akinori Komura, Kanagawa (JP)

(73) Assignee: FUJIFILM Business Innovation Corp., Tokyo (JP)

( * ) Notice: Subject to any disclaimer, the term of this patent is extended or adjusted under 35 U.S.C. 154(b) by 110 days.

This patent is subject to a terminal disclaimer.

(21) Appl. No.: 16/164,819

(22) Filed: Oct. 19, 2018

(65) Prior Publication Data

US 2019/0320963 A1 Oct. 24, 2019

(30) Foreign Application Priority Data

Apr. 23, 2018 (JP) .............................. JP2018-082465

(51) Int. Cl.
| | | |
|---|---|---|
| *A61B 5/16* | (2006.01) | |
| *H04R 1/32* | (2006.01) | |
| *G10L 25/78* | (2013.01) | |
| *G10L 25/51* | (2013.01) | |
| *A61B 5/00* | (2006.01) | |
| *A61B 5/024* | (2006.01) | |

(52) U.S. Cl.
CPC ............ *A61B 5/165* (2013.01); *A61B 5/4803* (2013.01); *A61B 5/486* (2013.01); *G10L 25/51* (2013.01); *G10L 25/78* (2013.01); *H04R 1/326* (2013.01); *A61B 5/024* (2013.01); *A61B 5/4035* (2013.01); *A61B 5/7278* (2013.01)

(58) Field of Classification Search
USPC ......................... 704/233, 246, 247, 251, 252
See application file for complete search history.

(56) References Cited

U.S. PATENT DOCUMENTS

| | | | | |
|---|---|---|---|---|
| 7,236,580 B1* | 6/2007 | Sarkar | ................... | H04M 3/567 379/202.01 |
| 2009/0282103 A1* | 11/2009 | Thakkar | ................. | H04N 7/147 709/204 |

FOREIGN PATENT DOCUMENTS

| | | |
|---|---|---|
| JP | 4487015 | 6/2010 |
| JP | 2011081504 | 4/2011 |
| JP | 2011120618 | 6/2011 |
| JP | 2012125382 | 7/2012 |
| JP | 2012125383 | 7/2012 |
| JP | 2012239666 | 12/2012 |
| JP | 2013046662 | 3/2013 |
| JP | 5480800 | 4/2014 |
| JP | 2014061079 | 4/2014 |

(Continued)

*Primary Examiner* — Leonard Saint Cyr
(74) *Attorney, Agent, or Firm* — JCIPRNET

(57) ABSTRACT

An information processing apparatus includes a first determination unit, a second determination unit, and a presentation unit. The first determination unit determines, based on biometric information of a speaker and a non-speaker, creativities of the speaker and the non-speaker, according to different indices. The second determination unit determines, according to the creativity of the speaker and the creativity of the non-speaker, a creativity of a group including the speaker and the non-speaker. The presentation unit presents the creativity of the group.

15 Claims, 10 Drawing Sheets

(56) References Cited

FOREIGN PATENT DOCUMENTS

| | | |
|---|---|---|
| JP | 5579125 | 8/2014 |
| JP | 5592323 | 9/2014 |
| JP | 5593473 | 9/2014 |
| JP | 5882169 | 3/2016 |
| JP | 2016091490 | 5/2016 |
| JP | 5944550 | 7/2016 |
| WO | 2016158515 | 10/2016 |

* cited by examiner

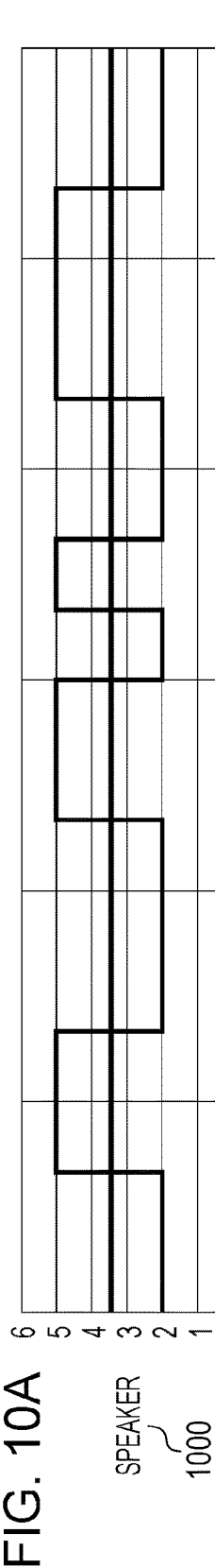
FIG. 10A SPEAKER 1000
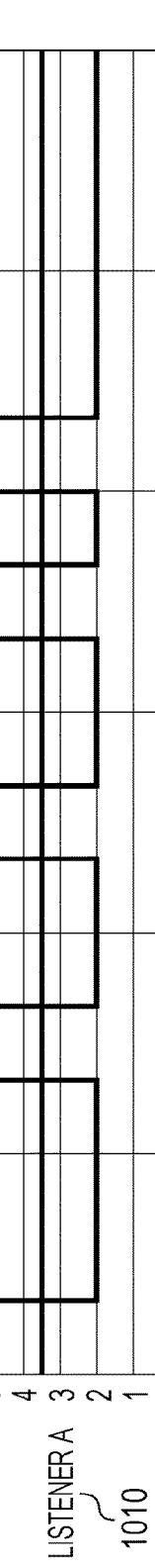
FIG. 10B LISTENER A 1010
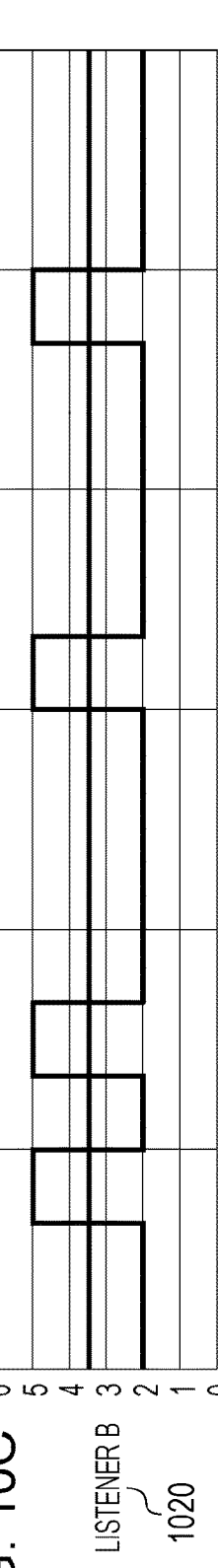
FIG. 10C LISTENER B 1020
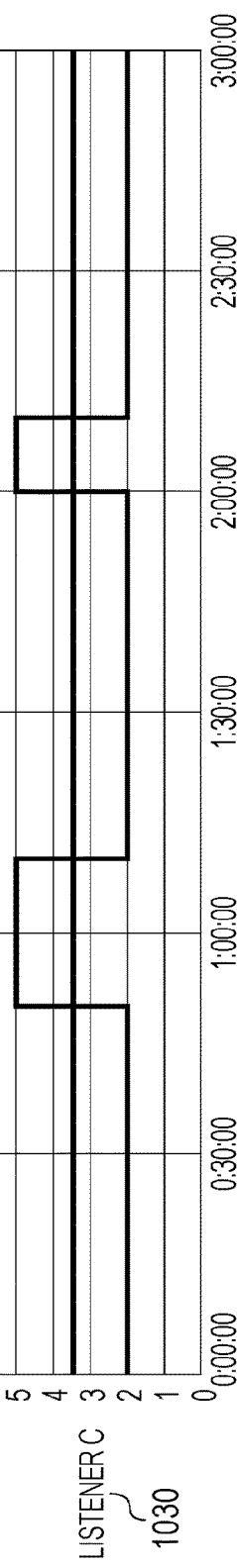
FIG. 10D LISTENER C 1030

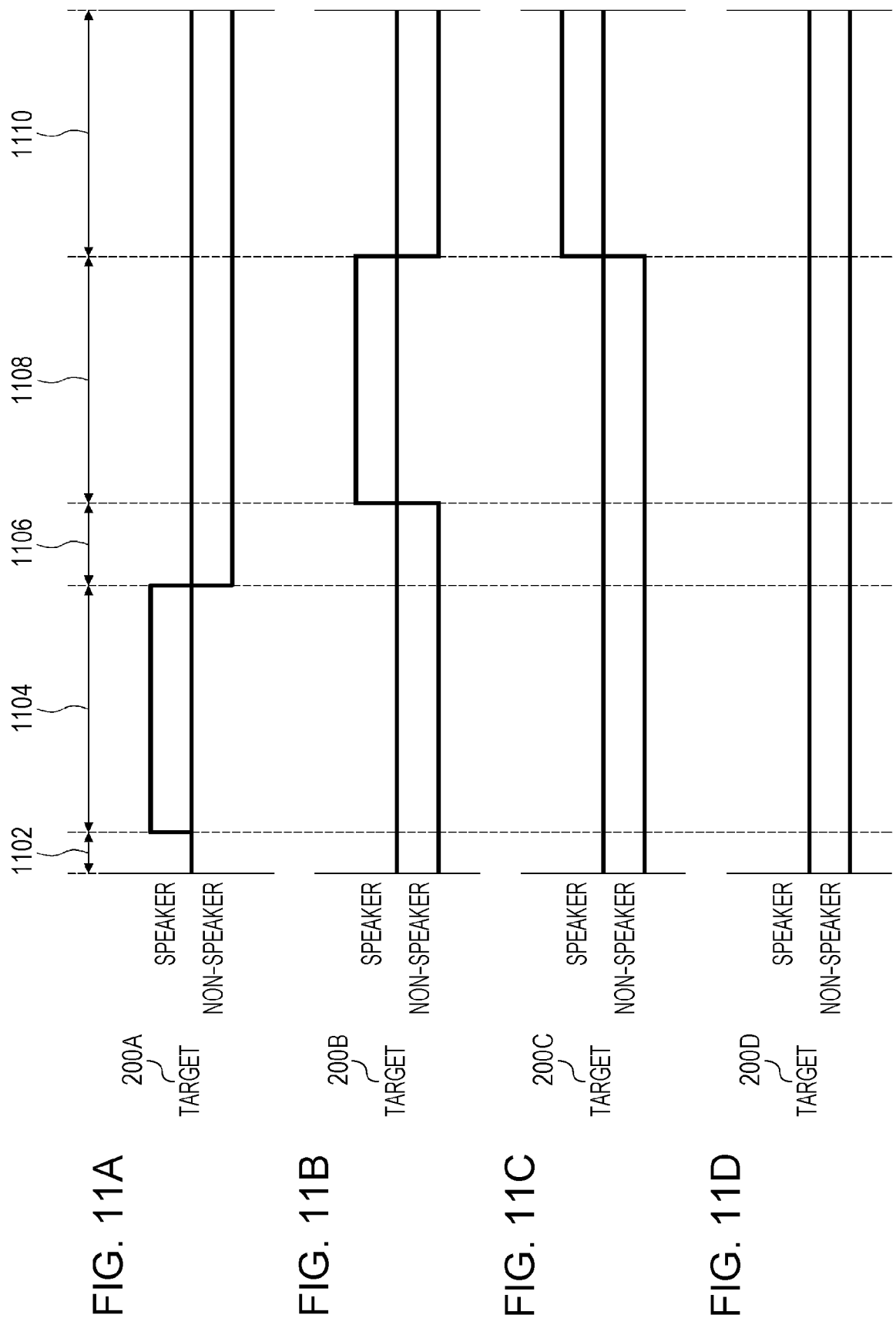

INFORMATION PROCESSING APPARATUS AND NON-TRANSITORY COMPUTER READABLE MEDIUM

CROSS-REFERENCE TO RELATED APPLICATIONS

This application is based on and claims priority under 35 USC 119 from Japanese Patent Application No. 2018-082465 filed Apr. 23, 2018.

BACKGROUND

(i) Technical Field

The present disclosure relates to an information processing apparatus and a non-transitory computer readable medium.

(ii) Related Art

To provide a conference system that is capable of improving the entire productivity of a conference held by a plurality of conference participants, a controller of the conference system including an individual productivity acquisition unit that acquires values of a plurality of individual productivities corresponding to pieces of biometric information correlated with a plurality of individual productivities calculated by a biometric measuring unit; an entire productivity calculation unit that calculates a value of the entire productivity based on the values of the plurality of individual productivities acquired by the individual productivity acquisition unit; a determination unit that determines whether or not the value of the entire productivity calculated by the entire productivity calculation unit is less than a predetermined threshold; and a driving unit that drives a stimulation providing unit such that in a case where the determination unit determines that the value of the entire productivity is less than the threshold, the stimulation providing unit provides the plurality of conference participants with stimulation to increase the value of the entire productivity, is disclosed in Japanese Unexamined Patent Application Publication No. 2016-091490.

To provide a conference support system that comprehensively evaluates the progress status of a conference and carries out proceedings, a feature that various sensing units detect the degree of liveliness and the degree of change as indices of the quality of the conference, a time productivity index is calculated based on the degree of liveliness, the degree of change, and the progress status of a schedule, feedback of a determination as to change of the proceedings or the like is performed according to conditions of the time productivity index, variability in the time productivity index is estimated for the feedback, presentation including prediction is provided slightly before the determination as to change of the proceedings is performed, and presentation of the feedback is performed using video, sound, lighting, air-conditions, and the like in a comprehensive manner, is disclosed in Japanese Unexamined Patent Application Publication No. 2011-081504.

SUMMARY

Aspects of non-limiting embodiments of the present disclosure relate to providing an information processing apparatus and a non-transitory computer readable medium capable of determining the creativity of a meeting at which a speaker and a non-speaker are present.

Aspects of certain non-limiting embodiments of the present disclosure address the above advantages and/or other advantages not described above. However, aspects of the non-limiting embodiments are not required to address the advantages described above, and aspects of the non-limiting embodiments of the present disclosure may not address advantages described above.

According to an aspect of the present disclosure, there is provided an information processing apparatus including a first determination unit, a second determination unit, and a presentation unit. The first determination unit determines, based on biometric information of a speaker and a non-speaker, creativities of the speaker and the non-speaker, according to different indices. The second determination unit determines, according to the creativity of the speaker and the creativity of the non-speaker, a creativity of a group including the speaker and the non-speaker. The presentation unit presents the creativity of the group.

BRIEF DESCRIPTION OF THE DRAWINGS

Exemplary embodiments of the present disclosure will be described in detail based on the following figures, wherein:

FIGS. 10A, 10B, 10C, and 10D are explanatory diagrams illustrating an example of processing according to an exemplary embodiment;

FIGS. 11A, 11B, 11C, and 11D are explanatory diagrams illustrating an example of processing according to an exemplary embodiment.

DETAILED DESCRIPTION

Exemplary embodiments of the present invention will be described below with reference to drawings.

Figure 1:
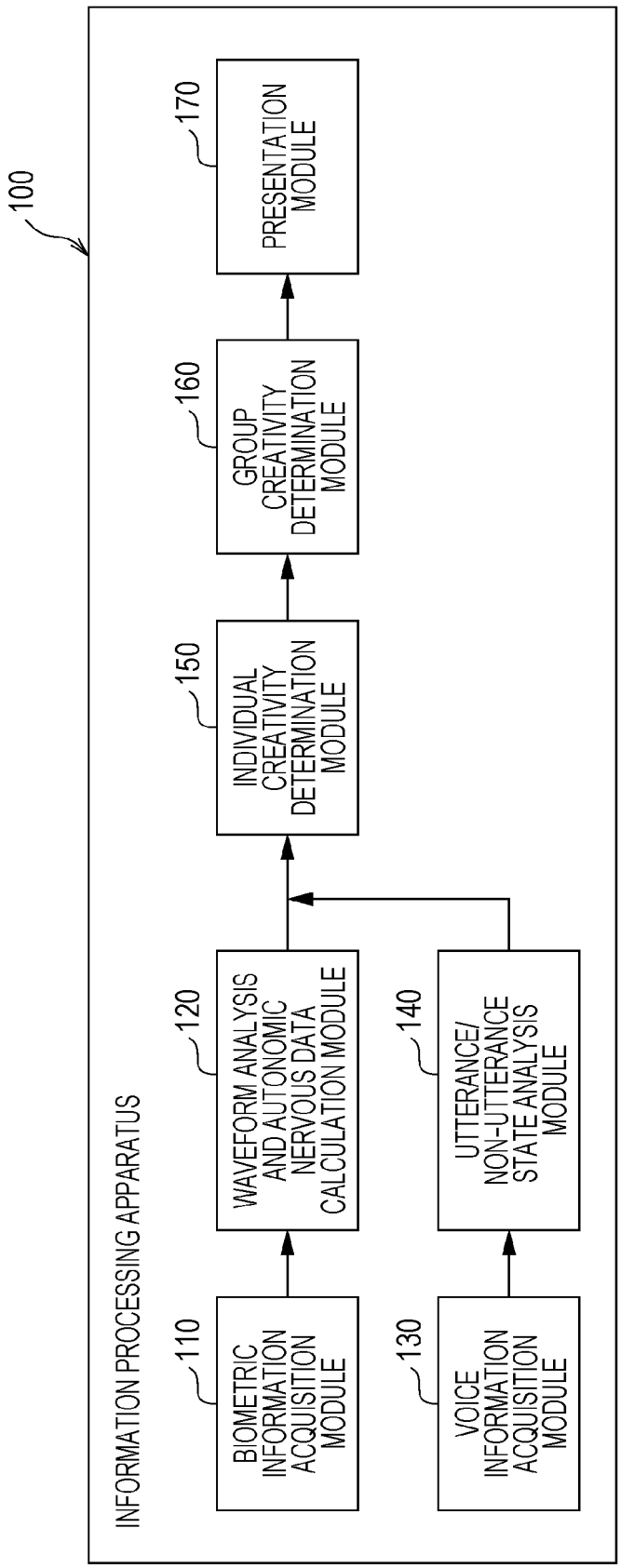
FIG. 1 is a conceptual module configuration diagram of an example of a configuration according to an exemplary embodiment.

FIG. 1 is a conceptual module configuration diagram illustrating an example of a configuration according to an exemplary embodiment.

In general, the term "module" refers to a component such as software (a computer program), hardware, or the like, which may be logically separated. Therefore, a module in an exemplary embodiment refers not only to a module in a computer program but also to a module in a hardware configuration. Accordingly, through exemplary embodiments, a computer program for causing the component to function as a module (a program for causing a computer to perform each step, a program for causing a computer to function as each unit, and a program for causing a computer to perform each function), a system, and a method are described. For convenience of explanation, the terms "store", "cause something to store", and other equivalent expressions will be used. When an exemplary embodiment relates to a computer program, the terms and expressions represent "causing a storing device to store" or "controlling a storing device to store". A module and a function may be associated on a one-to-one basis. In the actual implementation, however, one module may be implemented by one program, multiple modules may be implemented by one program, or one module may be implemented by multiple programs. Furthermore, multiple modules may be executed by one computer, or one module may be executed by multiple computers in a distributed computer environment or a parallel computer environment. Moreover, a module may include another module. In addition, hereinafter, the term "connection" may refer to logical connection (such as data transfer, instruction, cross-reference relationship between data, and logging in) as well as physical connection. The term "being predetermined" represents being set prior to target processing being performed. "Being predetermined" represents not only being set prior to processing in an exemplary embodiment but also being set even after the processing in the exemplary embodiment has started, in accordance with the condition and state at that time or in accordance with the condition and state during a period up to that time, as long as being set prior to the target processing being performed. When there are plural "predetermined values", the values may be different from one another, or two or more values (obviously, including all the values) may be the same. The term "in the case of A, B is performed" represents "a determination as to whether it is A or not is performed, and when it is determined to be A, B is performed", unless the determination of whether it is A or not is not required. Furthermore, in the case where objects such as "A, B, and C" are listed, they are exemplified as a list unless otherwise stated and a case where only one of them is selected (for example, only A is selected) is included.

Moreover, a "system" or an "apparatus" may be implemented not only by a plurality of computers, hardware, apparatuses, or the like connected through a communication unit such as a network (including one-to-one communication connection), but also by a single computer, hardware, apparatus, or the like. The terms "apparatus" and "system" are used as synonymous terms. Obviously, the term "system" does not include social "mechanisms" (social system), which are only artificially arranged.

Furthermore, for each process in a module or for individual processes in a module performing a plurality of processes, target information is read from a storing device and a processing result is written to the storing device after the process is performed. Therefore, the description of reading from the storing device before the process is performed or the description of writing to the storing device after the process is performed may be omitted. The storing device may be a hard disk (HD), a random access memory (RAM), an external storage medium, a storing device using a communication line, a register within a central processing unit (CPU), or the like.

An information processing apparatus 100 according to an exemplary embodiment determines the creativity of a meeting at which a speaker (also referred to as an utterer) and a non-speaker (also referred to as a non-utterer) are present. As in an example illustrated in FIG. 1, the information processing apparatus 100 includes a biometric information acquisition module 110, a waveform analysis and autonomic nervous data calculation module 120, a voice information acquisition module 130, an utterance/non-utterance state analysis module 140, an individual creativity determination module 150, a group creativity determination module 160, and a presentation module 170. A "meeting" may be a place, a situation, or the like where multiple people get together to talk and includes, for example, a conference, a consultation, a discussion, a greeting, and gathering. A case of a conference will be explained as an example. Furthermore, conference participants will be explained as an example of a speaker and a non-speaker in the conference.

As a conference diagnosis, determining the creativity of a group including multiple people is required. With the techniques described in Japanese Unexamined Patent Application Publication Nos. 2016-091490 and 2011-081504, the creativity of a group is not able to be determined accurately. That is, the degree of activeness and the degree of liveliness used in the techniques described in Japanese Unexamined Patent Application Publication Nos. 2016-091490 and 2011-081504 do not represent creativity. Regarding the degree of activeness and the degree of liveliness, a determination may be performed using the same index for speakers and non-speakers. Regarding a determination of creativity, however, the same index is not able to be used for speakers and non-speakers.

Thus, in an exemplary embodiment, determinations are performed as described below.

(1) Creativity of a speaker is determined based on a coefficient of variation of R-R intervals (coefficient of variation of electrocardiogram R-R intervals (CVRR)) and a component coefficient of variance high frequency (ccvHF).

(2) Creativity of a listener is determined based on a component coefficient of variance low frequency (ccvLF) and the ccvHF.

(3) Creativity of a group including the speaker and the listener is determined based on the creativity of the speaker and the creativity of the listener.

The CVRR represents the degree of activity, the ccvHF represents the degree of relaxation, and the ccvLF represents the degree of concentration. Calculation methods or the like for the CVRR, the ccvHF, and the ccvLF are described in detail, for example, in Japanese Patent Nos. 4487015, 5480800, 5579125, 5592323, 5593473, 5882169, and 5944550.

In (1) and (2), participants wear sensors (for heart rates and pulse waves), so that biometric information is acquired, and autonomic nervous information is calculated according to a waveform analysis program. At the same time, voice data of an individual is acquired from a directional microphone, and an utterance/non-utterance state is represented by 0/1 data. In the case where two types of degree of activeness of autonomic nerves corresponding to the speaker and the listener exceed thresholds, a creativity level is determined.

In (3), the creativity of a group is determined and displayed at specific time intervals, based on overlap between the ratio of a creative time of the speaker and the ratio of a creative time of the listener. The creativity level is represented according to the time ratio. A binary determination of whether the creativity is "present" or "absent" is performed according to a threshold.

Regarding "a generation concept of an idea", formation of an idea represents providing a new association to a variety of material information to generate a network structure of new material information.

"A generation process of an idea" represents a process in which a listener precisely receives information presented by a speaker and presents his/her own material information that is likely to be related to the information presented by the speaker, and a new association is formed between these pieces of information by the speaker, so that a new network structure of new material information is generated.

"A function of the degree of activity" represents providing a new association to a variety of material information.

"A function of the degree of relaxation" represents presenting a variety of material information (existing knowledge).

"A function of the degree of concentration" represents understanding and precisely receiving what a speaker speaks.

The biometric information acquisition module 110 is connected to the waveform analysis and autonomic nervous data calculation module 120. The biometric information acquisition module 110 acquires, with sensors, biometric information of conference participants (a speaker and a non-speaker). "Biometric information" includes, for example, a heart rate, a pulse rate, brain waves, and the like. In this example, a heart rate or pulse rate is preferably used. Sensors include, for example, a heart rate meter 210 in an example illustrated in FIG. 2.

The waveform analysis and autonomic nervous data calculation module 120 is connected to the biometric information acquisition module 110 and the individual creativity determination module 150. The waveform analysis and autonomic nervous data calculation module 120 acquires biometric information such as heart rate variability to calculate autonomic nervous information at a time. For example, the waveform analysis and autonomic nervous data calculation module 120 performs fast Fourier transform (FFT) of a heartbeat interval and a pulse wave interval for a certain period of time to calculate the degree of autonomic nervous activity. As the degrees of autonomic nervous activity, specifically, the CVRR, the ccvHF, and the ccvLF are calculated.

The voice information acquisition module 130 is connected to the utterance/non-utterance state analysis module 140. The voice information acquisition module 130 acquires uttered voices from a microphone to acquire utterance signals or non-utterance signals of conference participants.

The utterance/non-utterance state analysis module 140 is connected to the voice information acquisition module 130 and the individual creativity determination module 150. The utterance/non-utterance state analysis module 140 determines, based on voice information, whether a target is a speaker or a non-speaker. Specifically, the utterance/non-utterance state analysis module 140 acquires voice information of a conference participant to obtain data of an utterance/non-utterance state at a time. Specifically, data is obtained by allocating "1" and "0" to an utterance state and a non-utterance state, respectively. In this example, a non-utterer represents a person who belongs to a group as a target of the information processing apparatus 100 and is not a speaker. In general, non-speakers are listeners. However, for example, a non-utterer may be an absent-minded person. Obviously, a person may be a speaker at one time and a non-speaker at another time.

Furthermore, the utterance/non-utterance state analysis module 140 may determine a combination of a speaker and a non-speaker who listens to what the speaker speaks.

Furthermore, the utterance/non-utterance state analysis module 140 may determine, using a directional microphone, a combination of a speaker and a non-speaker who belong to a group. For example, people who are present at face-to-face positions may be determined to be a combination of a speaker and a non-speaker.

Furthermore, the utterance/non-utterance state analysis module 140 may determine the identity between voice data acquired by a microphone provided for a speaker and voice data acquired by a microphone provided for a non-speaker and may determine microphones that acquire the identical voice data to be a combination of a speaker and a non-speaker who belong to a group. For example, VoiStrap®, which will be described later with reference to FIG. 2, may be used.

The individual creativity determination module 150 is connected to the waveform analysis and autonomic nervous data calculation module 120, the utterance/non-utterance state analysis module 140, and the group creativity determination module 160. The individual creativity determination module 150 determines a creativity, based on a corresponding index, according to an utterance/non-utterance state of a conference participant, at a time. For example, the individual creativity determination module 150 determines creativities of a speaker and a non-speaker, based on biometric information of the speaker and the non-speaker, using different indices. A "non-speaker" represents a person who is not a speaker among people who join a conversation and is, in general, a listener. Specifically, the individual creativity determination module 150 acquires voice data (utterance/non-utterance state) at a corresponding time for each pulse, selects the degree of autonomic nervous activity corresponding to the state, determines whether or not the degree of autonomic nervous activity exceeds a threshold, and allocates a creativity level.

Furthermore, indices used by the individual creativity determination module 150 to determine creativities of a speaker and a non-speaker may be at least partially different. That is, in the case where multiple indices are used for determinations of the creativities of a speaker and a non-speaker, some of the indices may be different between the determinations of the creativities of the speaker and the non-speaker, whereas the other indices may be the same. For example, the degree of activity and the degree of relaxation may be used as indices for a determination of the creativity of a speaker, and the degree of concentration and the degree of relaxation may be used as indices for a determination of the creativity of a non-speaker. In this case, the degree of relaxation is used for both the determinations. However, the degree of activity is used for the determination as to the speaker, whereas the degree of concentration is used for the determination as to the non-speaker.

In the case where both the determinations of creativity are performed based on the degree of relaxation, different thresholds may be used for the speaker and the non-speaker.

For example, regarding the creativity of a speaker, a ratio may be obtained by accumulating creative times of the speaker present in a unit time interval and dividing the accumulated creative times by the unit time.

For example, regarding the creativity of a non-speaker, a ratio may be obtained by accumulating all the creative times of either one of all the non-speakers present in a unit time interval and dividing the accumulated creative times by the unit time.

The group creativity determination module 160 is connected to the individual creativity determination module 150 and the presentation module 170. The group creativity determination module 160 determines the creativity of a group including a speaker and a non-speaker, based on the creativity of the speaker and the creativity of the non-speaker. For example, the group creativity determination module 160 calculates the ratio of a creative time of a speaker and the ratio of a creative time of a non-speaker for a certain period of time (or a continuous utterance time of a person), and determines the creativity using threshold criteria for both the speaker and the non-speaker. Specifically, the group creativity determination module 160 determines the creativity of a group by plotting the creativity of a speaker and the creativity of a non-speaker (listener) for a certain period of time on a graph in which the creativity of the speaker is represented on the vertical axis and the creativity of the non-speaker (listener) is represented on the horizontal axis.

Furthermore, for a determination of the creativity of a group, the group creativity determination module 160 may use the creativity of a speaker at the time when the speaker makes an utterance and the creativity of a non-speaker at the time when a certain period of time has passed since the utterance of the speaker. This is because it takes for a non-speaker as a listener to understand the contents of the utterance. Furthermore, in the case where there is a change in the creativity of a non-speaker after a speaker makes an utterance, it is considered that the non-speaker as a listener understands the contents of the utterance. Therefore, the creativity of the non-speaker at the time when a change occurs in the creativity of the non-speaker after the speaker made an utterance may be used.

Furthermore, regarding a creativity during a time period in which there is no speaker, the group creativity determination module 160 may perform a determination based on the creativity of a group at the time when a speaker starts to speak. This is because the creativity of the group is not necessarily low even during a period in which no one speaks and a non-speaker may exhibit a creativity even during such a silent period. In this case, it is reasonable that a determination is performed based on the creativity of the group at the time when someone starts to speak after a state in which no one speaks as a creativity during a time period in which there is no speaker.

Furthermore, the group creativity determination module 160 may determine the creativity of a group, based on the ratio of time during which the creativity of a speaker is exhibited and the ratio of time during which the creativity of a non-speaker is exhibited. A time ratio represents the ratio of time during which creativity is exhibited to a predetermined time period.

In this case, in the case where there are multiple non-speakers, a statistic value of the time ratios of the non-speakers may be used. A "statistic value" represents, for example, the total sum, average, mode, median, maximum value, minimum value, and the like of the ratio of time during which one or more of the non-speakers exhibit creativity to a predetermined time period (a so-called logical sum), the ratio of times during which all the non-speakers exhibit creativity to the predetermined time period (a so-called logical product), and times during which non-speakers exhibit creativity in the predetermined time period.

Furthermore, the group creativity determination module 160 may determine the creativity of a group, based on a position defined by the creativity of a target speaker and the creativity of a target non-speaker in a coordinate space where the creativity of the speaker and the creativity of the non-speaker are represented on axes. This will be described later with reference to an example illustrated in FIG. 6.

Furthermore, the group creativity determination module 160 may determine the creativity of a group, based on a distance from the origin of a coordinate space where the creativity of a speaker and the creativity of a non-speaker are represented on axes to a position defined by the creativity of a target speaker and the creativity of a target non-speaker. This will be described later with reference to an example illustrated in FIG. 7.

Furthermore, the group creativity determination module 160 may determine that the creativity of a group during a time period in which there is no speaker is not determinable.

Furthermore, the group creativity determination module 160 may perform determination for each time period from the time when a non-speaker becomes a speaker to the time when the speaker becomes a non-speaker. That is, a section during which someone in a group is a speaker may be set as a time period during which a determination as to exhibition of the creativity of the group is able to be performed. In particular, only a time period during which a single person is a speaker may be set as a time period during which a determination as to exhibition of the creativity of the group is able to be performed.

Furthermore, the group creativity determination module 160 may determine the creativity of a group for a "time period from the time when a non-speaker becomes a speaker to the time when the speaker becomes a non-speaker", based on the time period and a predetermined period of time subsequent to the time period. It takes time for a non-speaker as a listener to understand the contents of an utterance, and therefore, the time period for which the determination as to exhibition of the creativity of a group is performed includes a later time period.

The presentation module 170 is connected to the group creativity determination module 160. The presentation module 170 presents the creativity of a group (visualization of the creativity of a group (so-called visualization)) determined by the group creativity determination module 160. Furthermore, the presentation module 170 may present the creativity of each individual determined by the individual creativity determination module 150. The presentation module 170 may present a time period during which creativity is exhibited or the ratio of time during which creativity is exhibited.

For example, the presentation module 170 may hold past plots on a graph indicating the creativity of a group obtained by the group creativity determination module 160 in a visualized state and indicate the trajectory of transition of the creativity of the group, together with the current creativity. Presentation may include output as three-dimensional (3D) video as well as display on a display device such as a liquid crystal display. Furthermore, a combination of printing by a printer, audio output by an audio output device such as a speaker, vibrations, and the like is also possible.

Figure 2:
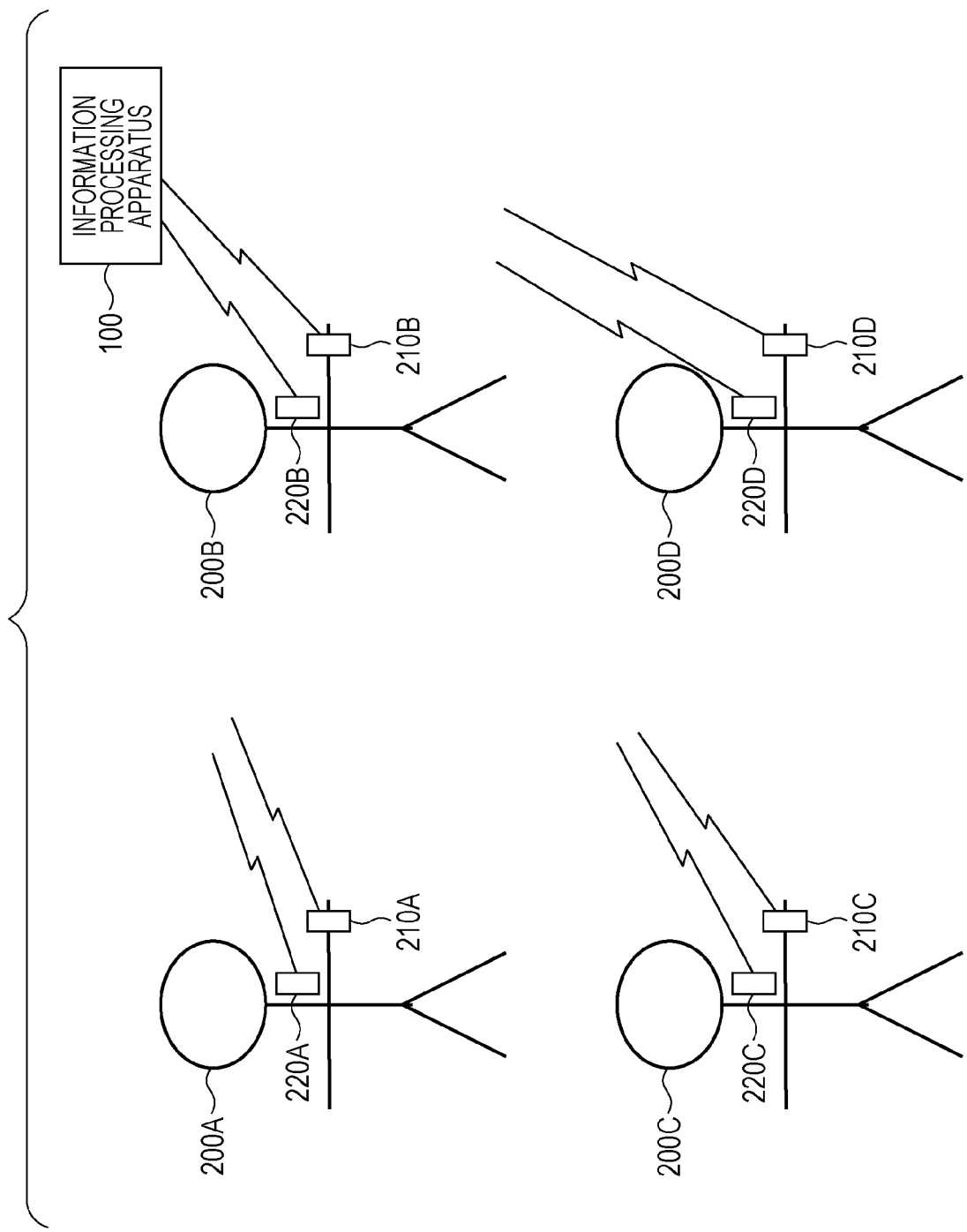
FIG. 2 is an explanatory diagram illustrating an example of a system configuration according to an exemplary embodiment.

FIG. 2 is an explanatory diagram illustrating an example of a system configuration according to an exemplary embodiment.

Targets 200 (targets 200A to 200D) are speakers or non-speakers (listeners) and wear the heart rate meters 210 (heart rate meters 210A to 210D) and microphones 220 (microphones 220A to 220D). The targets 200A to 200D (a group) are attending a meeting. In general, a person is a speaker and the other three people are listeners (non-speakers).

The heart rate meters 210 and the microphones 220 are connected to the information processing apparatus 100 via radio communication. The heart rate meters 210 are an example of sensors that detect biometric information of the targets 200. The microphones 220 are an example of devices that detect voice information of the targets 200.

The heart rate meters 210 each measure the heart rate by attaching a sensor to a chest or the like. Pulse waves, blood pressure variability, or the like may be measured by a pulse monitor of a wrist-band (wrist watch) type or an ear or finger clip type.

The microphones 220 receive voices of the targets 200 who are wearing the microphones 220. For example, the microphones 220 may be microphones used for VoiStrap. The VoiStrap including two microphones set up in a neck strap (string hanging around a neck) is able to discriminate the person who is wearing the VoiStrap from a nearby person, based on the difference in sound pressure of voice obtained by a microphone A provided near the mouth and a microphone B provided away from the mouth. That is, in the case where the same voice information as voice information detected by the microphone A that the target 200A is wearing is detected by the microphone B that a different person (the target 200B or the like) is wearing, the target 200A may be determined to be a speaker and the different person who is wearing the microphone B may be determined to be a non-speaker. Furthermore, in a simple manner, in the case where the microphone A detects voice information, the person who is wearing the microphone A may be determined to be a speaker and a different person may be determined to be a non-speaker.

As described above, a speaker and a non-speaker may be identified using directional microphones, instead of the microphones 220.

The information processing apparatus 100 receives information from the heart rate meters 210 and the microphones 220 and presents the creativity of a group including the targets 200A to 200D. The creativity of a group may be presented in real time or batch processing may be performed after the meeting is finished. Furthermore, a user who uses the information processing apparatus 100 may be a user such as a researcher, a boss of the targets 200, or the like or a target 200 in the group.

Figure 3:
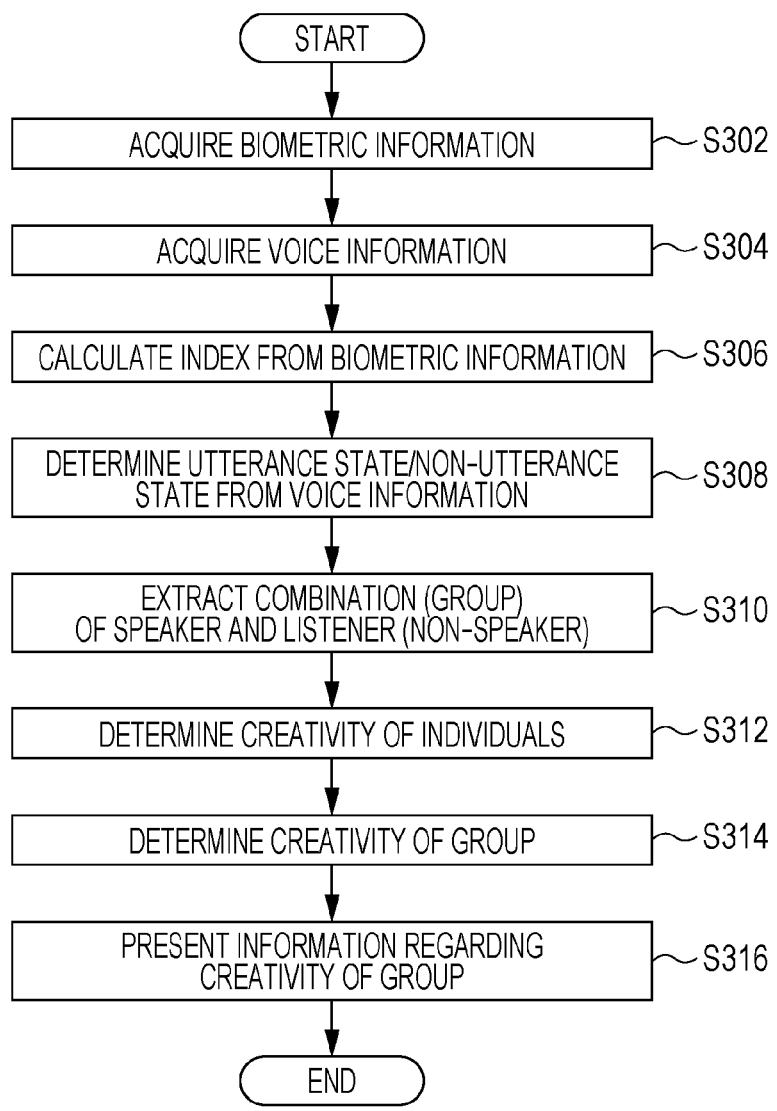
FIG. 3 is a flowchart illustrating an example of a process according to an exemplary embodiment.

FIG. 3 is a flowchart illustrating an example of a process according to an exemplary embodiment.

In step S302, the biometric information acquisition module 110 acquires biometric information from the heart rate meters 210.

In step S304, the voice information acquisition module 130 acquires voice information from the microphones 220.

In step S306, the waveform analysis and autonomic nervous data calculation module 120 calculates indices from the biometric information. As described above, the degree of activity, the degree of relaxation, and the degree of concentration are used as indices.

In step S308, the utterance/non-utterance state analysis module 140 determines, based on the voice information, whether the current state is an utterance state or a non-utterance state.

In step S310, the utterance/non-utterance state analysis module 140 extracts a combination (group) of a speaker and a listener (non-speaker). That is, the utterance/non-utterance state analysis module 140 determines a combination of a speaker and a non-speaker. As described above, with the use of the VoiStrap, in the case where a pair (or a team) for a conversation is formed, microphones for both of the pair or team members receive voices. Therefore, it may be determined, based on matching waveforms of the two pieces of voice information, that microphones 220 of corresponding IDs are adjacent to each other for the conversation.

However, when multiple pieces of voice information are input at the same time, it is determined that the combination of corresponding IDs is not a pair (or team) for a conversation. For example, in the case where there is a dispute, the pair in the conversation may make an utterance at the same time. However, this situation is determined to be an error. In the flow of the entire conversation time, a combination for the conversation is sequentially identified, and errors occurring momentarily may be avoided by following a previous proper combination for a certain period of time.

Furthermore, a group formed may be determined using a position identification device such as a global positioning system (GPS).

In contrast, by using only a technique for position identification such as a GPS, the result of a determination as to a pair for a conversation is more unreliable than the errors described above.

Furthermore, the orientation of the face or the like of a conference participant may be extracted by photographing the face or the like of the conference participant with a camera. In the case where different pairs each having a conversation in adjacent places (for example, there are one pair of the target 200A and the target 200B and the other pair of the target 200C and the target 200D in FIG. 2), a difference occurs in the sound pressure, depending on the distance between the conference participants and the orientation of the faces of the conference participants (there is a small sound pressure between people who do not form a pair). Therefore, based on the difference in the sound pressure, the pair members may be separated from each other. In the case where a person is talking with a different person with the same distance and sound pressure as the pair, there are overlapping utterances. Therefore, IDs of them may be determined not to be a pair.

Furthermore, in the case where multiple pieces of voice information overlap due to a dispute, determinations are repeated while results of determination as to a pair being followed until a time several seconds after the determination time for a certain period of time. If the overlap disappears, for example, after several seconds, the voice information may be determined to be a pair (a pair several seconds ago is inherited). If the overlap lasts for a long time (several tens of seconds), the voice information may be determined not to be a pair.

In step S312, the individual creativity determination module 150 determines the creativity of individuals. Explanation will be provided below with reference to examples illustrated in FIGS. 4 and 5.

Figure 4:
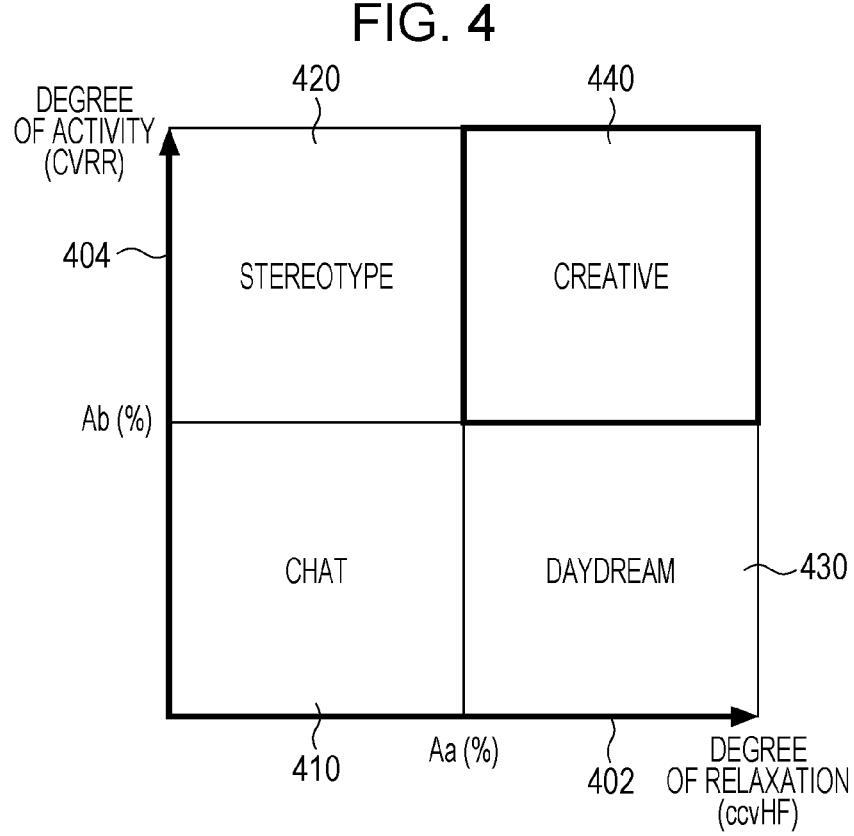
FIG. 4 is an explanatory diagram illustrating an example of processing according to an exemplary embodiment.

FIG. 4 is an explanatory diagram illustrating an example of processing according to an exemplary embodiment. The example illustrated in FIG. 4 represents a determination as to the creativity of a speaker. In FIG. 4, the horizontal axis represents the degree of relaxation (ccvHF), and the vertical axis represents the degree of activity (CVRR). It is determined, based on a threshold Aa and a threshold Ab, whether the creativity of the speaker corresponds to chat 410, stereotype 420, daydream 430, or creative 440. Specifically, it may be determined whether the creativity of the speaker corresponds to the chat 410, the stereotype 420, the daydream 430, or the creative 440 by comparing the ratio of a period with a high degree of relaxation (a period with a predetermined value or more) to a certain period with the threshold Aa and comparing the ratio of a period with a high degree of activity (a period with a predetermined value or more) to the certain period with the threshold Ab.

The chat 410 indicates a state in which the degree of activity and the degree of relaxation of the speaker are both low and narrow discussion brings about no new idea.

The stereotype 420 indicates a state in which a high degree of activity of the speaker enables linking of information but a low degree of relaxation causes less variety of material information to be presented and impedes generation of broader ideas.

The daydream 430 indicates a state in which a high degree of relaxation allows a variety of material information to be brought up in the conversation but a low degree of activity of the speaker prevents sufficient linking of information and impedes formation of an idea.

The creative 440 indicates a state in which a high degree of activity and a high degree of relaxation allow a variety of material information to be brought up in the conversation and those pieces of material information are linked together so that a new idea is generated.

In the case where the degree of relaxation is less than the threshold Aa and the degree of activity is less than the threshold Ab, the creativity of the speaker is determined to be the chat 410.

In the case where the degree of relaxation is less than the threshold Aa and the degree of activity is equal to or more than the threshold Ab, the creativity of the speaker is determined to be the stereotype 420.

In the case where the degree of relaxation is equal to or more than the threshold Aa and the degree of activity is less than the threshold Ab, the creativity of the speaker is determined to be the daydream 430.

In the case where the degree of relaxation is equal to or more than the threshold Aa and the degree of activity is equal to or more than the threshold Ab, the creativity of the speaker is determined to be the creative 440.

The individual creativity determination module 150 may determine at least whether or not the creativity of the speaker corresponds to the creative 440. Obviously, the individual creativity determination module 150 may determine whether the creativity of the speaker corresponds to the chat 410, the stereotype 420, or the daydream 430, as well as the determination of whether or not the creativity of the speaker corresponds to the creative 440.

Figure 5:
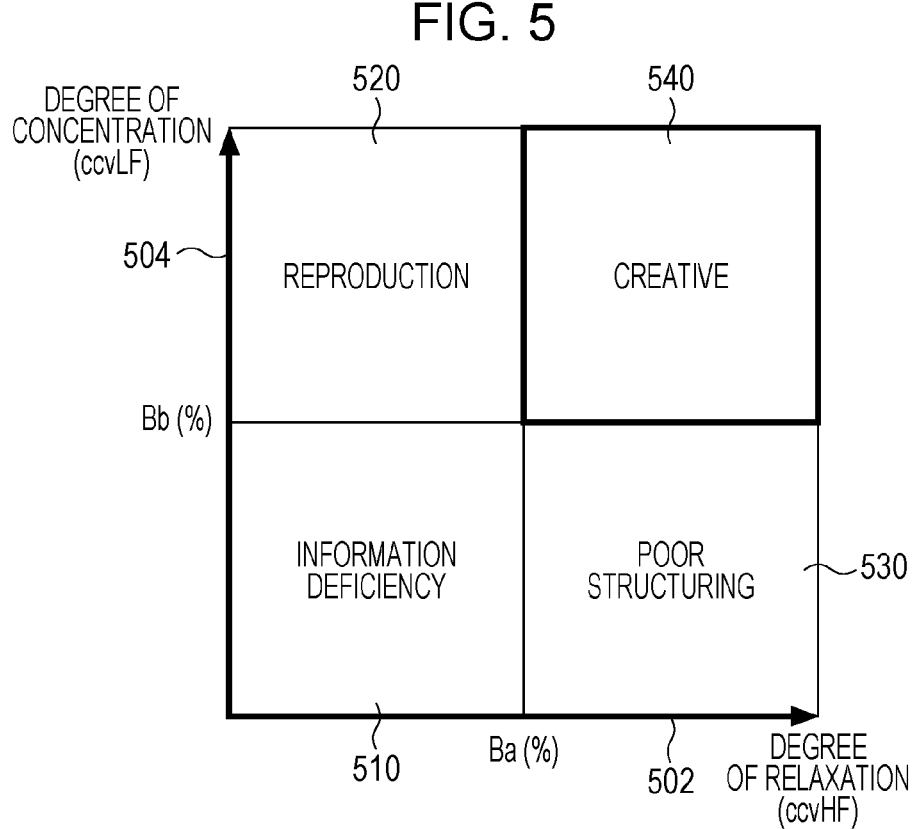
FIG. 5 is an explanatory diagram illustrating an example of processing according to an exemplary embodiment.

FIG. 5 is an explanatory diagram illustrating an example of processing according to an exemplary embodiment. The example illustrated in FIG. 5 represents a determination as to the creativity of a non-speaker (listener). In FIG. 5, the horizontal axis represents the degree of relaxation (ccvHF), and the vertical axis represents the degree of concentration (ccvLF). It is determined, based on a threshold Ba and a threshold Bb, whether the creativity of the non-speaker corresponds to information deficiency 510, reproduction 520, poor structuring 530, or creative 540. Specifically, it may be determined whether the creativity of the non-speaker corresponds to the information deficiency 510, the reproduction 520, the poor structuring 530, or the creative 540 by comparing the ratio of a period with a high degree of relaxation (a period with a predetermined value or more) to a certain period with the threshold Ba and comparing the ratio of a period with a high degree of concentration (a period with a predetermined value or more) to the certain period with the threshold Bb. As in the example illustrated in FIG. 4, the degree of relaxation is represented on the horizontal axis. However, the threshold Ba may be different from the threshold Aa (however, a case where the threshold Ba is equal to the threshold Aa is not excluded). For example, the threshold Aa may be higher than the threshold Ba.

The information deficiency 510 indicates a state in which a low degree of concentration makes the listener unable to precisely receive what the speaker speaks and a low degree of relaxation causes no material information to be added and impedes generation of an idea.

The reproduction 520 indicates a state in which a high degree of concentration enables the listener to precisely receive what the speaker speaks but a low degree of relaxation makes the listener unable to present a variety of material information and impedes expansion of ideas.

The poor structuring 530 indicates a state in which a low degree of concentration makes the listener unable to precisely receive what the speaker speaks and to obtain a proper form of an idea even with a high degree of relaxation enabling the listener to add a variety of material information.

The creative 540 indicates a state in which a high degree of concentration enables the listener to precisely receive what the speaker speaks and a high degree of relaxation enables expansion of ideas by adding a variety of material information.

In the case where the degree of relaxation is less than the threshold Ba and the degree of concentration is less than the threshold Bb, the creativity of the non-speaker is determined to be the information deficiency 510.

In the case where the degree of relaxation is less than the threshold Ba and the degree of concentration is equal to or more than the threshold Bb, the creativity of the non-speaker is determined to be the reproduction 520.

In the case where the degree of relaxation is equal to or more than the threshold Ba and the degree of the concentration is less than the threshold Bb, the creativity of the non-speaker is determined to be the poor structuring 530.

In the case where the degree of relaxation is equal to or more than the threshold Ba and the degree of concentration is equal to or more than the threshold Bb, the creativity of the non-speaker is determined to be the creative 540.

The individual creativity determination module 150 may determine at least whether or not the creativity of the non-speaker corresponds to the creative 540. Obviously, the individual creativity determination module 150 may determine whether the creativity of the non-speaker corresponds to the information deficiency 510, the reproduction 520, or the poor structuring 530, as well as the determination of whether or not the creativity of the non-speaker corresponds to the creative 540.

In step S314, the group creativity determination module 160 determines the creativity of a group. This will be explained below with reference to an example illustrated in FIG. 6.

Figure 6:
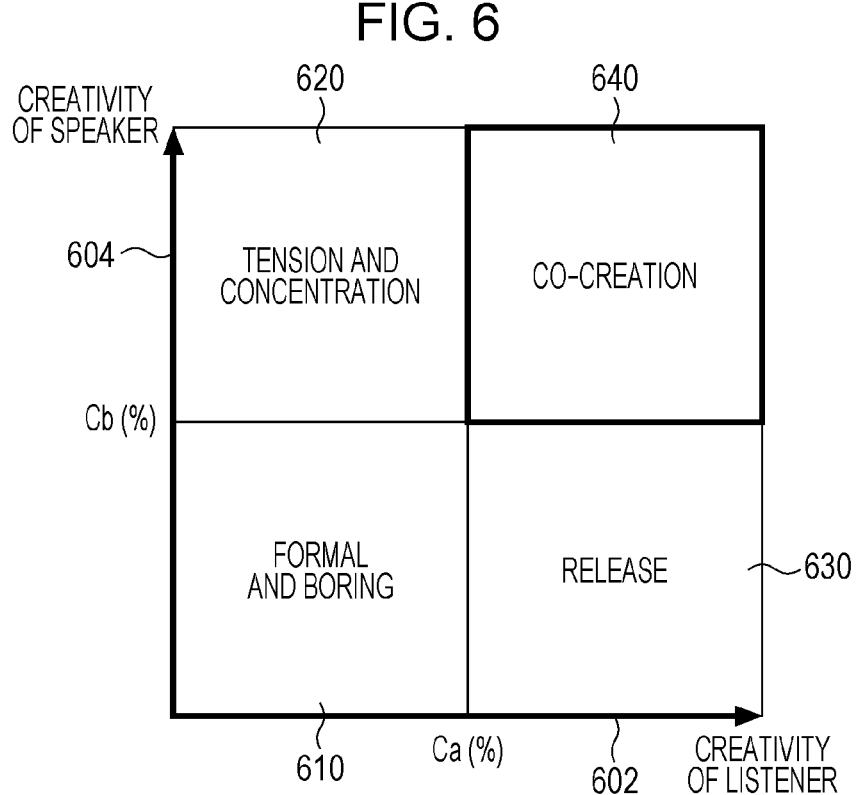
FIG. 6 is an explanatory diagram illustrating an example of processing according to an exemplary embodiment.

FIG. 6 is an explanatory diagram illustrating an example of processing according to an exemplary embodiment. In FIG. 6, the horizontal axis represents the value of the creativity of a listener (non-speaker) and the vertical axis represents the value of the creativity of a speaker. It is determined, based on a threshold Ca and a threshold Cb, whether the creativity of the group corresponds to formal and boring 610, tension and concentration 620, release 630, and co-creation 640. Specifically, it may be determined whether the creativity of the group including a speaker and a listener corresponds to the formal and boring 610, the tension and concentration 620, the release 630, or the co-creation 640 by comparing the ratio of a period during which the listener is recognized as being creative (a determination result in step S312 for the listener) to a certain period with the threshold Ca and comparing the ratio of period during which the speaker is recognized as being creative (a determination result in step S312 for the speaker) to the certain period with the threshold Cb.

The formal and boring 610 indicates a formal state with a low creativity of the speaker and a low creativity of the listener and nothing is generated. For example, a committee, a liaison meeting, or the like corresponds to the formal and boring 610.

The tension and concentration 620 indicates a state in which a high creativity of the speaker and a low creativity of the listener end in a speech and conversation is not widened (or expanded). For example, a discussion, a presentation, or the like corresponds to the tension and concentration 620.

The release 630 indicates a state in which a low creativity of the speaker and a high creativity of the listener prevent the direction (axis) of a discussion from being fixed and personal daydreams keep being released. For example, a chat or the like corresponds to the release 630.

The co-creation 640 indicates a state in which a high creativity of the speaker and a high creativity of the listener bring about a co-creation state of the conversation and a new idea is generated. For example, a dialog (may also be dialogue) or the like corresponds to the co-creation 640.

In the case where the value of the creativity of the listener is less than the threshold Ca and the value of the creativity of the speaker is less than the threshold Cb, the creativity of the group is determined to be the formal and boring 610.

In the case where the value of the creativity of the listener is less than the threshold Ca and the value of the creativity of the speaker is equal to or more than the threshold Cb, the creativity of the group is determined to be the tension and concentration 620.

In the case where the value of the creativity of the listener is equal to or more than the threshold Ca and the value of the creativity of the speaker is less than the threshold Cb, the creativity of the group is determined to be the release 630.

In the case where the value of the creativity of the listener is equal to or more than the threshold Ca and the value of the creativity of the speaker is equal to or more than the threshold Cb, the creativity of the group is determined to be the co-creation 640.

The group creativity determination module 160 may determine at least whether or not the creativity of the group corresponds to the co-creation 640. Obviously, the group creativity determination module 160 may determine whether the creativity of the group corresponds to the formal and boring 610, the tension and concentration 620, or the release 630, as well as the determination of whether or not the creativity of the group corresponds to the co-creation 640.

In step S316, the presentation module 170 presents information regarding the creativity of the group. Specifically, the presentation module 170 presents a determination result in step S314.

Figure 7:
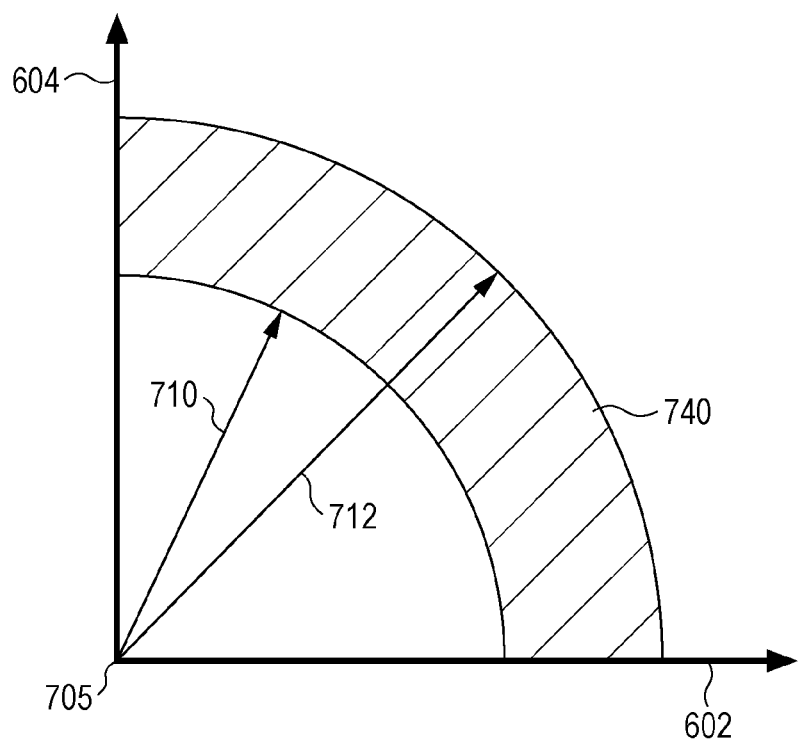
FIG. 7 is an explanatory diagram illustrating an example of processing according to an exemplary embodiment.

FIG. 7 is an explanatory diagram illustrating an example of processing according to an exemplary embodiment. The creativity of a group is determined as described in the example illustrated in FIG. 6. However, the determination of the creativity of a group is not necessarily performed as described above. The determination of the creativity of a group may be performed based on a graph in an example illustrated in FIG. 7. That is, a creativity axis 602 for a listener and a creativity axis 604 for a speaker are set as in the example illustrated in FIG. 6, and a creativity in a region that is equal to or more than a distance 710 away from an origin 705 and less than or equal to a distance 712 away from the origin 705 may be determined to be co-creation 740.

Figure 8:
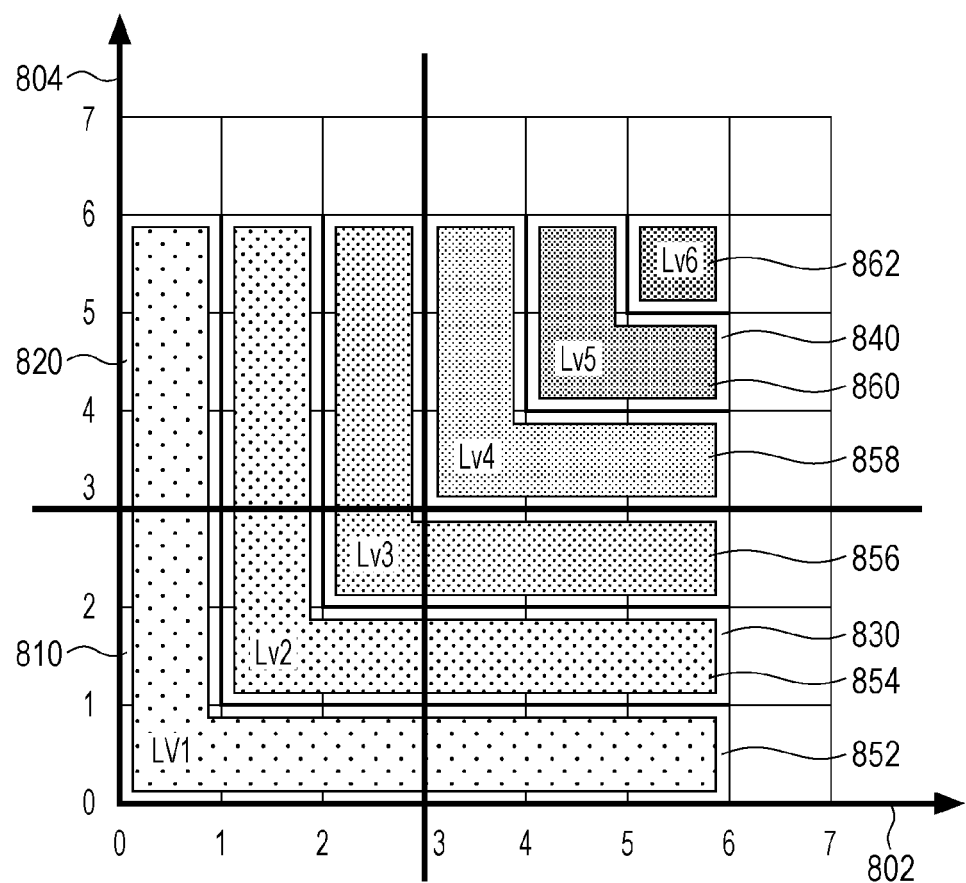
FIG. 8 is an explanatory diagram illustrating an example of processing according to an exemplary embodiment.

FIG. 8 is an explanatory diagram illustrating an example of processing according to an exemplary embodiment. The creativities of a speaker, a listener, and a group are determined as described in the examples illustrated in FIGS. 4, 5, 6, and 7. However, the creativities of a speaker, a listener, and a group are not necessarily determined as described above. The creativity of a speaker, a listener, and a group may be determined based on a graph as in an example illustrated in FIG. 8. That is, a horizontal axis 802 and a vertical axis 804 are set as in the examples illustrated in FIGS. 4, 5, 6, and 7. A determination of which L-shaped region (level 1: 852, level 2: 854, level 3: 856, level 4: 858, level 5: 860, or level 6: 862) data is plotted in is performed. In the case where data is plotted at the level 4 or a higher level (level 4: 858, level 5: 860, or level 6: 862, in a region 840), the creativity of a speaker or a listener may be determined to be "creative" (corresponding to the creative 440 in the example of FIG. 4 or the creative 540 in the example of FIG. 5) or the creativity of a group may be determined to be "co-creation" (corresponding to the co-creation 640 in the example of FIG. 6).

The level 1: 852 represents a level with no creativity, and is, for example, a case where only understanding of the current situation and confirmation of the locus of responsibility are performed and the conversation might go back. The level 2: 854 represents, for example, a case where only an object or a reason for failure is presented and the conversation does not proceed. The level 3: 856 represents, for example, a case where only a generalization or existing knowledge is introduced. The level 4: 858 represents, for example, a case where new noticing or finding occurs in the conversation. The level 5: 860 represents, for example, a case where a new policy or measures are presented in the conversation. The level 6: 862 is a level with the highest creativity and represents, for example, a case where an intention to start a new action is confirmed in the conversation.

Figure 9A:
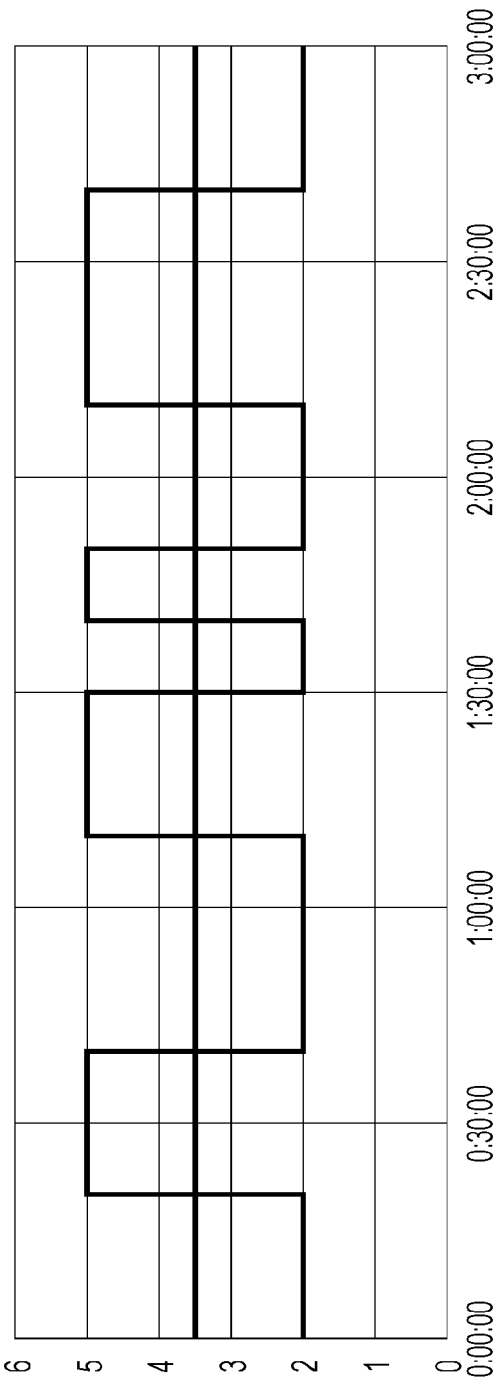
FIGS. 9A and 9B are explanatory diagrams illustrating an example of processing according to an exemplary embodiment.
Figure 9B:
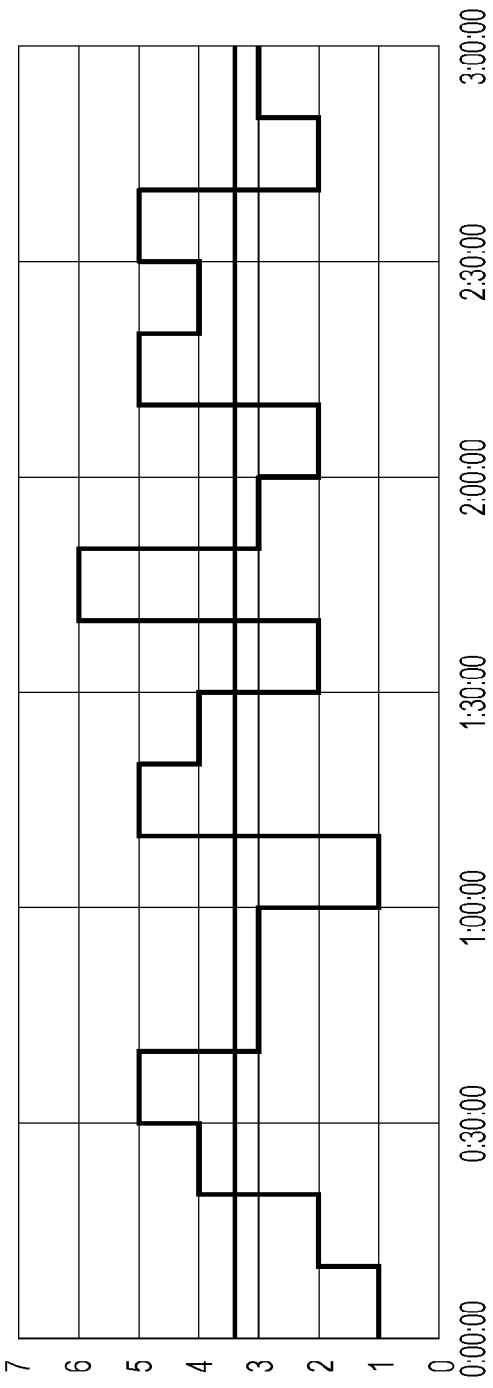

FIGS. 9A and 9B are explanatory diagrams illustrating an example of processing according to an exemplary embodiment. Results of a determination of the creativity of a speaker or a listener obtained by the individual creativity determination module 150 (step S312) are indicated on the time axis. Specifically, transition for three minutes (0:00:00 to 3:00:00) is illustrated.

FIG. 9A illustrates results of binary determination (in the graph, "5" represents presence of creativity and "2" represents absence of creativity). FIG. 9B illustrates results of six-valued determination (in the graph, six stages from 1 to 6, where values equal to or more than 3.5 represent presence of creativity and values less than 3.5 represent absence of creativity).

As illustrated in the example of FIGS. 9A and 9B, transition between "presence of creativity" and "absence of creativity" occurs as time goes by.

FIGS. 10A, 10B, 10C, and 10D are explanatory diagrams illustrating an example of processing according to an exemplary embodiment. Results of a determination of the creativity of each conference participant (speaker or listener) obtained by the group creativity determination module 160 (step S314) are indicated on the time axis. Specifically, transition for three minutes (0:00:00 to 3:00:00) in a target time period is indicated. During the three minutes, the utterance/non-utterance state analysis module 140 (step S308) determines one participant to be a speaker 1000 and the other three participants to be listeners (a listener A 1010, a listener B 1020, and a listener C 1030). That is, the three minutes is a time period in which the speaker 1000 makes continuous utterances.

The creativity of the speaker 1000 during the three minutes is 44% (the sum of times for which the creativity of the speaker 1000 is determined to be "presence of creativity" is 1 minute and 19 seconds), the creativity of the listener A 1010 during the same three minutes is 28% (the sum of times for which the creativity of the listener A 1010 is determined to be "presence of creativity" is 50 seconds), the creativity of the listener B 1020 during the three minutes is 22% (the sum of times for which the creativity of the listener B 1020 is determined to be "presence of creativity" is 40 seconds), and the creativity of the listener C 1030 during the three minutes is 17% (the sum of times for which the creativity of the listener C 1030 is determined to be "presence of creativity" is 30 seconds).

In the case where the creativity of a group is determined as in FIG. 6, the creativity of the speaker 1000 is 44%, and therefore, this value may be compared with the threshold Cb (vertical axis in FIG. 6).

In contrast, there are three listeners, and therefore, how the creativities of listeners (horizontal axis in FIG. 6) are to be determined is an issue. Specifically, in the case where there are listeners with a high creativity and a low creativity, how the creativity of the group is to be determined is an issue.

Thus, the total sum, average, mode, median, maximum value, minimum value, or the like of the values of the creativities of all the listeners may be used. Furthermore, a statistic value (the total sum, average, mode, median, maximum value, minimum value, or the like) to be used may be determined in accordance with the distribution of values of creativities of listeners. For example, a difference between the maximum value and the minimum value of the values of creativities is calculated. In the case where the difference is equal to or more than a predetermined value, the maximum value of the listeners may be used. Specifically, if a person exhibits a high creativity, conditions for creating a new idea are met as the field of a conversation. Therefore, by regarding the definition of a word "creativity of a group" as the "creativity of the field of a conversation", the value of the creativity of a person with the maximum value (a person with the highest value of creativity among multiple listeners) may be used. This is because the use of the average of the listeners may cause underestimation.

Furthermore, as described below, calculation may be performed by logical operation on the time axis. Values obtained by such calculation methods are also included in examples of statistic values.

The logical product of sections during which the creativities of the listener A 1010, the listener B 1020, and the listener C 1030 are exhibited in the period of three minutes (called "listener average creativity") is 22%. That is, the logical product represents the ratio of the time period during which creativities of all the listener A 1010, the listener B 1020, and the listener C 1030 are determined to be "presence of creativity" to the period of three minutes (target time period).

The logical sum of sections during which the creativities of the listener A 1010, the listener B 1020, and the listener C 1030 are exhibited in the period of three minutes (called "listener integrated creativity") is 56%. That is, the logical sum represents the ratio of the time period during which the creativity of one or more of the listener A 1010, the listener B 1020, and the listener C 1030 is determined to be "presence of creativity" to the period of three minutes (target time period).

The value of the listener average creativity and the value of the listener integrated creativity may be applied to the horizontal axis of FIG. 6.

FIGS. 11A, 11B, 11C, and 11D are explanatory diagrams illustrating an example of processing according to an exemplary embodiment. Conference participants are categorized into speakers and non-speakers by the utterance/non-utterance state analysis module 140 (step S308). A specific example will be described below.

In a section 1102, all the four participants 200A to 200D are non-speakers.

In a section 1104, the target 200A is a speaker, and the target 200B, the target 200C, and the target 200D are non-speakers.

In a section 1106, all the four participants 200A to 200D are non-speakers.

In a section 1108, the target 200B is a speaker, and the target 200A, the target 200C, and the target 200D are non-speakers.

In a section 1110, the target 200C is a speaker, and the target 200A, the target 200B, and the target 200D are non-speakers.

As described above, all the conference participants may be non-speakers (a silent state, that is, a time period in which there no speaker). Thus, the group creativity determination module 160 performs determination as described below.

In this case, it may be determined that the creativity of the group is not determinable. In particular, at the beginning of the conference like the section 1102, it is preferable that the creativity of the group is not determinable.

Furthermore, a determination may be performed based on the creativity of the group at the time when a speaker starts to speak. That is, based on the creativity of the group at the timing when the speaker starts to speak, a feedback to the creativity in the silent state is performed. Specifically, the value of the creativity of the group in the section 1108 (the target 200B is a speaker) is used as the creativity of the group in the section 1106.

If the current topic brought up when the speaker starts to speak (when someone starts to talk and silence is broken) is the same as the previous topic, the creativity of a non-speaker is maintained. However, if the previous thought (topic) of the non-speaker does not correspond to the contents of the utterance of the speaker, the creativity of the non-speaker is considered to be lowered. Obviously, the non-speaker may not listen to what the speaker speaks at all and indulge in daydreams. In such a case, the ccvHF is high and the ccvLF is low. Therefore, even if results of the creativity of the group obtained in the case where all the conference participants are non-speakers (a silent state, that is, a time period in which there is no speaker) are different from results of the creativity of the group when a speaker starts to speak, the results of the creativity of the group at the time when the speaker starts to speak are regarded as the results of the creativity of the group in the case where all the conference participants are non-speakers (a silent state, that is, a time period in which there is no speaker).

Thus, regarding how the state before an utterance occurs is to be evaluated, a high creativity results in a high ccvLF and a high ccvHF unless a non-speaker indulges in daydreams, and therefore, the creativity of the non-speaker is obtained correctly. In this case, the creativity of the group is determined based on the distance from the origin, instead of determination of creativity based on coordinate plots of a creativity score CS of the speaker (creativity of speaker) and a creativity score CL of the non-speaker (creativity of listener) (see FIG. 7).

However, this may be a creativity of a release type. Therefore, at the moment when someone speaks about his/her own daydreams, the creativity of the other non-speakers is likely to be lowered.

However, if the non-speakers have different creativities before someone makes an utterance, the creativities of the non-speakers are often creative, from the point of view of presence of various ideas being thought. Even in the case where a non-speaker has a different opinion, if the non-speaker understands the utterance, the creativity of the non-speaker remains creative. In addition, even if the non-speaker holds his/her own opinion of objection, the creativity of the non-speaker is maintained. Therefore, it may be considered that a situation in which the creativity of the non-speaker is lowered by the utterance indicates that there is a change from the previous state.

In contrast, making an utterance represents the fact that the utterer was creative in the previous non-utterance state. In this case, the creativity of the group may be determined based on the distance from the origin of the coordinates of the creativity of the speaker and the creativity of the listener (see FIG. 7).

Therefore, the creativity of the group in the case where a speaker starts to speak from a silent state is to be determined based on the distance from the origin, as explained in the example illustrated in FIG. 7, instead of based on thresholds provided for the creativity of the speaker and the creativity of the listener.

However, there is an issue about whether the creativity of the group is actually high in the case where the creativity of the speaker is high but the creativity of the non-speaker is low (for example, a score is level 1 or 10% but not 0).

Taking into consideration the above issues, the distance from the origin (see FIG. 7) and the method for plotting on coordinates based on threshold determination of two elements (see FIG. 6) are both used.

Furthermore, when there is no speaker, creativity is not necessarily determined, and it may be determined that creativity is "not determinable".

It takes some time for a non-speaker to understand what a speaker speaks. Thus, to determine the creativity of a group, the creativity of the speaker at the time when the speaker makes an utterance and the creativity of the non-speaker at the time when a certain period of time has passed since the utterance of the speaker may be used.

When the creativity of a non-speaker increases while listening to what a speaker speaks depends on the person. However, a non-speaker may finally understand what a speaker speaks after the speaker finishes his/her utterance and the creativity of the non-speaker may increase accordingly. In this case, elements (the creativity of the speaker and the creativity of the non-speaker) to be used for a determination of the creativity of a group do not increase at the same time. However, when a conversation is taken from a macro point of view, the speaker makes an utterance with a high creativity and the creativity of the non-speaker (listener) increases in response to the utterance. Therefore, the conversation is to be determined to be a conversation with a high creativity.

Thus, the creativity of a group is determined based on a period including a time required for a non-speaker to increase the creativity after an utterance by a person is finished.

Specifically, creativity may be determined based on a certain period of time, not for each heat beat. At this time, for example, a certain period of time to be used for determination is a time twice (or three times, four times, or more) the continuous utterance time of a speaker, and the determination is performed based on the utterance start time as a start point. In this case, an end point is the time when the same time as the utterance time has passed since ending of the utterance. For example, in the case where an utterance starts at 13:10:30 and ends at 13:11:10 (the continuous utterance time is 40 seconds), the start point for the determination is 13:10:30 and the end point is 13:11:50, which is 40 seconds after 13:11:10. The creativity of this section is represented by the ratio of a creative time determined based on thresholds corresponding to the states of all the conference participants (utterance and non-utterance).

Furthermore, taking into consideration that the creativity of a non-speaker increases a certain period of time after an utterance, to determine the creativity of a group by associating the state of the creativity of the non-speaker with the utterance, a section until the time when the certain period of time has passed since the utterance end time may be defined as a target for each of continuous utterances.

For example, the length of this section may be set to twice (or three times, four times, or more) the length of the utterance time or a period to the time when the next utterance following the utterance is finished.

Furthermore, as another method, the creativity of a group may be determined by combining the creativity of a non-speaker occurring after an utterance is finished with the creativity at the time when the speaker makes the utterance.

At this time, the creativity of a group is determined by combining the creativity of a non-speaker for a section from the ending of the utterance of the speaker to the time when the same time as the utterance time of the speaker has passed with the creativity while the speaker is making the utterance. In this case, the creativity of a person who has become the next speaker does not represent the creativity at a non-utterance time, and therefore is not used for the determination of the creativity of the group.

Figure 12:
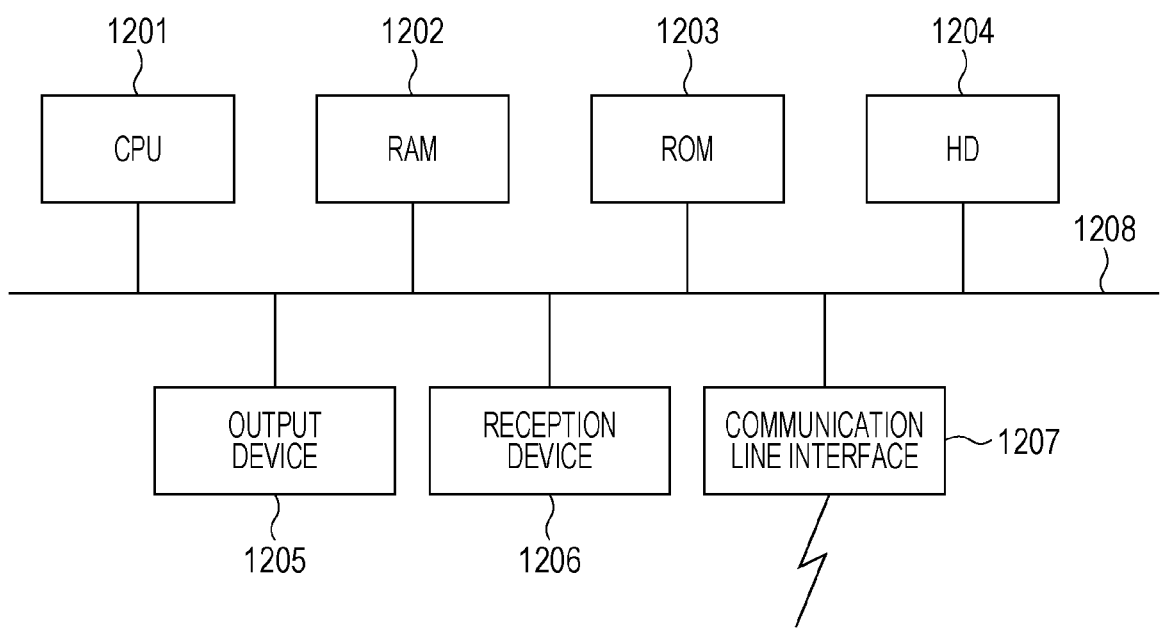
FIG. 12 is a block diagram illustrating an example of a hardware configuration of a computer implementing an exemplary embodiment.

A hardware configuration of a computer that executes a program according to an exemplary embodiment is, as illustrated in FIG. 12, a general computer, and specifically, a computer or the like that may serve as a personal computer or a server. That is, as a specific example, a CPU 1201 is used as a processing unit (arithmetic unit), and a RAM 1202, a read only memory (ROM) 1203, and an HD 1204 are used as a storing device. For example, a hard disk or a solid state drive (SSD) may be used as the HD 1204. The hardware configuration includes the CPU 1201 that executes programs such as the biometric information acquisition module 110, the waveform analysis and autonomic nervous data calculation module 120, the voice information acquisition module 130, the utterance/non-utterance state analysis module 140, the individual creativity determination module 150, the group creativity determination module 160, the presentation module 170, and the like, the RAM 1202 that stores the programs and data, the ROM 1203 that stores a program or the like for activating the computer, the HD 1204, which is an auxiliary storing device (may be a flash memory or the like) that stores biometric information, voice information, determination results, and the like, a reception device 1206 that receives data in accordance with an operation (including action, voice, a sight line, and the like) performed by a user for a keyboard, a mouse, a touch screen, a microphone, a camera (including a sight line detection camera or the like), an output device 1205 such as a cathode ray tube (CRT), a liquid crystal display, or a speaker, a communication line interface 1207 for allowing connection with a communication network such as a network interface card, and a bus 1208 for allowing data exchange among the above units. Multiple computers having the above configuration may be connected to one another via a network.

The foregoing exemplary embodiment that relates to a computer program is implemented by causing a system of the above hardware configuration to read the computer program, which is software, in cooperation of software and hardware resources.

The hardware configuration illustrated in FIG. 12 illustrates a configuration example. An exemplary embodiment is not limited to the configuration illustrated in FIG. 12 as long as a configuration which may execute modules explained in the exemplary embodiment is provided. For example, part of the modules may be configured as dedicated hardware (for example, an application specific integrated circuit (ASIC) or the like), part of the modules may be arranged in an external system in such a manner that they are connected via a communication line, or the system illustrated in FIG. 12 which is provided in plural may be connected via a communication line in such a manner that they operate in cooperation. Furthermore, in particular, part of the modules may be incorporated in a personal computer, a portable information communication device (including a mobile phone, a smart phone, a mobile device, and a wearable computer), an information electronic appliance, a robot, a copying machine, a facsimile machine, a scanner, a printer, or a multifunction device (an image processing device having two or more functions of a scanner, a printer, a copying machine, a facsimile machine, and the like).

Regarding comparison processing in the above description of the foregoing exemplary embodiment, those referred to as "not less than", "not more than", "larger than", or "smaller (less) than" may also be referred to as "larger than", "smaller (less) than", "not less than", or "not more than", respectively, unless no contradiction arises in combinations thereof.

The programs described above may be stored in a recording medium and provided or may be supplied through communication. In this case, for example, the program described above may be considered as a disclosure of "a computer-readable recording medium that records a program".

"A computer-readable recording medium that records a program" represents a computer-readable recording medium that records a program to be used for installation, execution, and distribution of the program.

A recording medium is, for example, a digital versatile disc (DVD), including "a DVD-R, a DVD-RW, a DVD-RAM, etc.", which are the standards set by a DVD forum, and "a DVD+R, a DVD+RW, etc.", which are the standards set by a DVD+RW, a compact disc (CD), including a read-only memory (CD-ROM), a CD recordable (CD-R), a CD rewritable (CD-RW), etc., a Blu-ray™ Disc, a magneto-optical disk (MO), a flexible disk (FD), a magnetic tape, a hard disk, a ROM, an electrically erasable programmable read-only memory (EEPROM™), a flash memory, a RAM, a secure digital (SD) memory card, or the like.

The entire or part of the above-mentioned program may be recorded in the above recording medium, to be stored and distributed. Furthermore, the program may be transmitted through communication, for example, a wired network or a wireless communication network used for a local area network (LAN), a metropolitan area network (MAN), a wide area network (WAN), the Internet, an intranet, an extranet, or the like, or a transmission medium of a combination of the above networks. Alternatively, the program or a part of the program may be delivered by carrier waves.

The above-mentioned program may be the entire or part of another program or may be recorded in a recording medium along with a separate program. Further, the program may be divided into multiple recording media and recorded. The program may be recorded in any format, such as compression or encryption, as long as the program may be reproduced.

The foregoing description of the exemplary embodiments of the present disclosure has been provided for the purposes of illustration and description. It is not intended to be exhaustive or to limit the disclosure to the precise forms disclosed. Obviously, many modifications and variations will be apparent to practitioners skilled in the art. The embodiments were chosen and described in order to best explain the principles of the disclosure and its practical applications, thereby enabling others skilled in the art to understand the disclosure for various embodiments and with the various modifications as are suited to the particular use contemplated. It is intended that the scope of the disclosure be defined by the following claims and their equivalents.

What is claimed is:

1. An information processing apparatus comprising:
at least a processor, configured to:
determine, based on biometric information of a speaker and a non-speaker, creativities of the speaker and the non-speaker, according to different indices;
determine a creativity of a group including the speaker and the non-speaker according to a ratio of time during which the creativity of the speaker is exhibited, a ratio of time during which the creativity of the non-speaker is exhibited, the creativity of the speaker at a time when the speaker makes an utterance, the creativity of the non-speaker at a time when a certain period of time has passed since the utterance by the speaker are used, and a position defined by the creativity of a target speaker and the creativity of a target non-speaker in a coordinated space in which creativity of the speaker and the creativity of the non-speaker are presented on axes; and
present the creativity of the group.

2. The information processing apparatus according to claim 1,
wherein a creativity for a time period in which there is no speaker is determined based on the creativity of the group at a time when a speaker starts to speak.

3. The information processing apparatus according to claim 1,
wherein indices to determine the creativity of the speaker and the creativity of the non-speaker are at least partially different.

4. The information processing apparatus according to claim 3,
wherein to determine a creativity according to a degree of relaxation, different thresholds are used for the speaker and the non-speaker.

5. The information processing apparatus according to claim 1,
wherein in a case where there are a plurality of non-speakers, a statistic value of the ratio of the time for the plurality of non-speakers is used.

6. The information processing apparatus according to claim 1,
wherein the processor determines the creativity of the group, based on a distance from an origin of the coordinate space in which the creativity of the speaker and the creativity of the non-speaker are represented on the axes to a position defined by the creativity of a target speaker and the creativity of a target non-speaker.

7. The information processing apparatus according to claim 1,
wherein the processor determines that the creativity of the group for a time period in which there is no speaker is not determinable.

8. The information processing apparatus according to claim 1, wherein the processor is further configured to:
determine, based on voice information, whether a target is a speaker or a non-speaker.

9. The information processing apparatus according to claim 8,
wherein the processor determines a combination of a speaker and a non-speaker as a listener who listens to what the speaker speaks.

10. The information processing apparatus according to claim 9,
wherein the processor determines, using a directional microphone, a combination of a speaker and a non-speaker forming the group.

11. The information processing apparatus according to claim 9,
wherein the processor determines whether or not voice data acquired by a microphone provided for the speaker is identical to voice data acquired by a microphone provided for the non-speaker, and determines microphones that acquire identical voice data to be a combination of the speaker and the non-speaker forming the group.

12. The information processing apparatus according to claim 8,
wherein the processor performs a determination for each time period from a time when a non-speaker becomes a speaker to a time when the speaker becomes a non-speaker.

13. The information processing apparatus according to claim 12,
wherein the processor determines the creativity of the group for the time period, based on the time period and a predetermined period of time subsequent to the time period.

14. An information processing apparatus comprising:
first determination means for determining, based on biometric information of a speaker and a non-speaker, creativities of the speaker and the non-speaker, according to different indices;
second determination means for determining a creativity of a group including the speaker and the non-speaker according to a ratio of time during which the creativity of the speaker is exhibited, a ratio of time during which the creativity of the non-speaker is exhibited, the creativity of the speaker at a time when the speaker makes an utterance, the creativity of the non-speaker at a time when a certain period of time has passed since the utterance by the speaker are used, and a position defined by the creativity of a target speaker and the creativity of a target non-speaker in a coordinated space in which creativity of the speaker and the creativity of the non-speaker are presented on axes; and
presentation means for presenting the creativity of the group.

15. A non-transitory computer readable medium storing a program causing a computer to execute a process for information processing, the process comprising:
determining, based on biometric information of a speaker and a non-speaker, creativities of the speaker and the non-speaker, according to different indices;
determining a creativity of a group including the speaker and the non-speaker according to a ratio of time during which the creativity of the speaker is exhibited, a ratio of time during which the creativity of the non-speaker is exhibited, the creativity of the speaker at a time when the speaker makes an utterance, the creativity of the non-speaker at a time when a certain period of time has passed since the utterance by the speaker are used, and a position defined by the creativity of a target speaker and the creativity of a target non-speaker in a coordinated space in which creativity of the speaker and the creativity of the non-speaker are presented on axes; and
presenting the creativity of the group.

* * * * *